US011337440B2

(12) United States Patent
Boursier et al.

(10) Patent No.: US 11,337,440 B2
(45) Date of Patent: May 24, 2022

(54) ASSEMBLY OF AT LEAST ONE VEGETABLE PROTEIN AND AT LEAST ONE DAIRY PROTEIN

(71) Applicants: ROQUETTE FRERES, Lestrem (FR); INGREDIA, Arras (FR); INSTITUT NATIONAL DE RECHERCHE POUR L'AGRICULTURE, L'ALIMENTATION ET L'ENVIRONNMENT, Paris (FR)

(72) Inventors: Bernard Boursier, Violaines (FR); Emmanuelle Moretti, Lille (FR); Guillaume Ribadeau-Dumas, Verlinghem (FR); Saliha Belaid, Joinville le Pont (CM); Alain Riaublanc, Ligne (FR); Jacques Gueguen, La Chapelle sur Erdre (FR); Anne Lepoudere, Guer (FR); Jean-Jacques Snappe, Festubert (FR); Isabelle Colin, Anzin Saint Aubin (FR)

(73) Assignees: ROQUETTE FRERES, Lestrem (FR); INGREDIA, Arras (FR); INSTITUT NATIONAL DE RECHERCHE POUR L'AGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 261 days.

(21) Appl. No.: 14/429,797

(22) PCT Filed: Sep. 23, 2013

(86) PCT No.: PCT/FR2013/052215
§ 371 (c)(1),
(2) Date: Mar. 20, 2015

(87) PCT Pub. No.: WO2014/044990
PCT Pub. Date: Mar. 27, 2014

(65) Prior Publication Data
US 2015/0237885 A1 Aug. 27, 2015

(30) Foreign Application Priority Data

Sep. 21, 2012 (FR) ..................................... 12 58903

(51) Int. Cl.
| | |
|---|---|
| *A23J 3/08* | (2006.01) |
| *C07K 14/415* | (2006.01) |
| *C07K 14/47* | (2006.01) |
| *A23J 1/00* | (2006.01) |
| *A23J 1/20* | (2006.01) |
| *A23J 3/14* | (2006.01) |
| *A23J 3/06* | (2006.01) |
| *A23L 33/185* | (2016.01) |
| *A23L 33/19* | (2016.01) |

(52) U.S. Cl.
CPC ................. *A23J 3/08* (2013.01); *A23J 1/006* (2013.01); *A23J 1/20* (2013.01); *A23J 3/06* (2013.01); *A23J 3/14* (2013.01); *A23L 33/185* (2016.08); *A23L 33/19* (2016.08); *C07K 14/415* (2013.01); *C07K 14/47* (2013.01)

(58) Field of Classification Search
CPC ...... A23J 3/08; A23J 3/14; A23J 1/006; A23J 1/20; C07K 14/415; C07K 14/47; C07K 1/02
See application file for complete search history.

(56) References Cited

U.S. PATENT DOCUMENTS

| | | | |
|---|---|---|---|
| 3,873,751 A | | 3/1975 | Arndt |
| 3,995,070 A | * | 11/1976 | Nagasawa ................. A23J 3/10 426/580 |
| 4,378,376 A | | 3/1983 | Wagner et al. |
| 5,514,655 A | | 5/1996 | DeWille et al. |
| 5,547,927 A | | 8/1996 | Cope et al. |
| 2003/0104033 A1 | | 6/2003 | Lai et al. |
| 2006/0204454 A1 | * | 9/2006 | Veerman ............... A23C 9/1307 424/50 |
| 2008/0020125 A1 | * | 1/2008 | Ganjyal ................ A23L 13/426 426/657 |
| 2008/0226810 A1 | * | 9/2008 | Passe ........................ A23J 1/14 426/656 |

FOREIGN PATENT DOCUMENTS

| | | |
|---|---|---|
| CN | 101756106 | 6/2010 |
| CN | 102458159 | 5/2012 |
| EP | 2623109 A1 | 8/2013 |
| FR | 2 497 364 A1 | 7/1982 |
| JP | 5495771 A | 7/1979 |
| JP | A06078685 A | 3/1994 |
| JP | A06335364 A | 12/1994 |
| JP | 2006508160 A | 3/2006 |
| WO | 92/15696 A1 | 9/1992 |
| WO | 2004049819 A2 | 6/2004 |
| WO | 2007/004883 A2 | 1/2007 |
| WO | 2007/017572 A1 | 2/2007 |
| WO | 2008/001183 A2 | 1/2008 |
| WO | 2008/052062 A1 | 5/2008 |

(Continued)

OTHER PUBLICATIONS

R. Hoover et al.: "Composition, structure, functionality and chemical modification of legume starches: a review" Can. J. Physiol. Pharmacol., 69, pp. 79-92). 1991 (Hoover R. (1991).

(Continued)

*Primary Examiner* — Jyoti Chawla
(74) *Attorney, Agent, or Firm* — Nixon & Vanderhye

(57) ABSTRACT

A method for producing an assembly of at least one dairy protein and at least one vegetable protein, and the assembly obtained by the method. Also, the uses of the assembly, in particular in the food processing field.

2 Claims, 1 Drawing Sheet

(56) References Cited

FOREIGN PATENT DOCUMENTS

| WO | WO-2009113858 A1 * | 9/2009 | ............ A23L 33/30 |
|----|----|----|----|
| WO | 2009/155557 A2 | 12/2009 | |
| WO | 2010/126353 A1 | 11/2010 | |
| WO | 2010/126362 A1 | 11/2010 | |
| WO | 2010/131952 A1 | 11/2010 | |
| WO | 2012043688 A1 | 9/2011 | |

OTHER PUBLICATIONS

C-L Heydley et al., entitled "Developing novel pea starches" Proceedings of the Symposium of the Industrial Biochemistry and Biotechnology Group of the Biochemical Society, 1996, pp. 77-87.

J. Gueguen from "Legume seed protein, processing, and end product characteristics", 1983 in Proceedings of European congress on plant proteins for human food (3-4) pp. 267-304).

International Search Report, dated Jan. 13, 2014, from corresponding PCT application, pp. 1 -2.

Chinese Office Action, dated Dec. 28, 2015; Application No. 2013800489948, pp. 1-21.

Aug. 2, 2017, JP communication issued for related JP application No. 2015-532491, pp. 1-20.

Schuck et al., "Déshydratation des laits enrichis en caséine micellaire par microfiltration; comparaison des propriétés des poudres obtenues avec celles d'une poudre de lait ultra-pro pre", "Dehydration of milks enriched with micellar casein by microfiltration; comparison of the properties of the powders obtained with those of an ultra-clean milk powder", Lait, 1994, vol. 74, pp. 47-63, with English Abstract provided.

Euston et al., "The Emulsifying Properties of Commercial Milk Protein Products in Simple Oil-in-Water Emulsions and in a Model food System", Journal of Food Science, 2000, vol. 65, No. 6.

Test Report filed by the Opponent, "Production of Milk Protein—Bean Protein Assembles", Jan. 22, 2021, English Machine Translation provided.

"Physico-Chemical Analysis Report, Test within the framework of Patent EP2897474B1", Jan. 29, 2021, English Machine Translation provided.

* cited by examiner

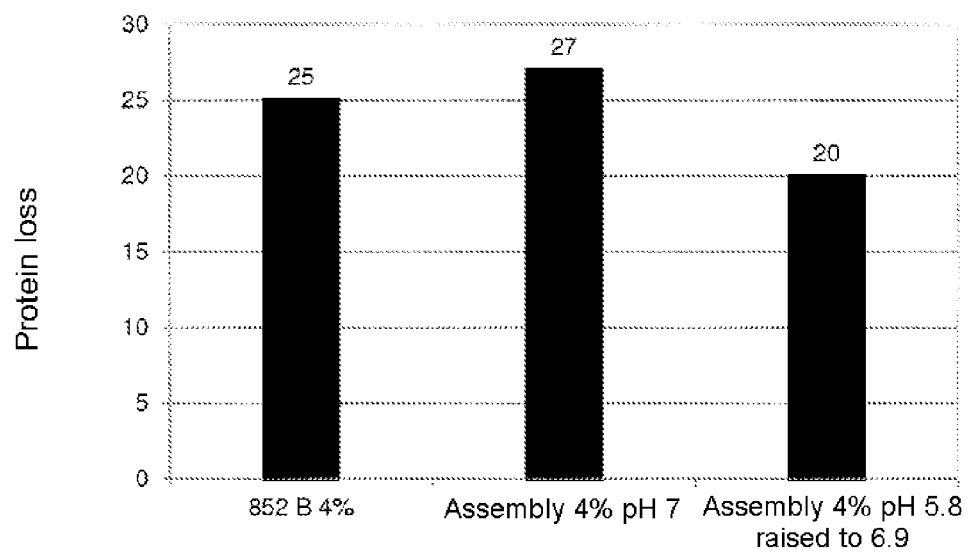

ASSEMBLY OF AT LEAST ONE VEGETABLE PROTEIN AND AT LEAST ONE DAIRY PROTEIN

FIELD OF THE INVENTION

The subject of the present invention is a process for producing an assembly of at least one dairy protein and at least one vegetable protein. The subject of the present invention is also the assembly that can be obtained by means of said process, and also the uses thereof, in particular in the food-processing field.

TECHNICAL BACKGROUND

Along with carbohydrates and lipids, proteins constitute a considerable part of our diet. Consumed proteins generally come either from an animal origin (meat, fish, eggs, dairy products, etc.), or from a vegetable origin (cereals, leguminous plants, etc.).

Their nutritional role is to provide amino acids and energy, which are substrates required for the synthesis of the body's proteins.

Proteins are composed of a sequence of amino acids. There are 20 amino acids, 9 of which are essential to humans, since the body is not able to synthesize them, and they must therefore be provided by the diet.

In the conventional approach, the quality of proteins is evaluated on the basis of their essential amino acid content. It is in particular known that, as a general rule, proteins of animal origin are richer in certain essential amino acids than vegetable proteins.

Milk proteins are of advantageous nutritional interest; on the other hand, they are expensive and this can curb their use. Manufacturers therefore seek substitute proteins, and vegetable proteins are attractive substitute proteins.

Numerous patent applications already describe the use of vegetable proteins for replacing all or some of the proteins of animal origin in foods. However, the substitute proteins currently available on the market do not necessarily possess functionally optimal and advantageous properties, equivalent to the functional properties of the functional protein ingredients of animal origin.

Proteins play an important role regarding the organoleptic quality of many fresh or manufactured foods, for instance the consistency and the texture of meat and meat-based products, of milk and derivatives, of pasta and of bread. These qualities of foods very frequently depend on the structure, the physicochemical properties and the functional properties of the protein constituents of the foods.

The term "functional properties" of food ingredients means, in the present application, any non-nutritional property which influences the utility of an ingredient in a food. These various properties contribute to obtaining the desired final characteristics of the food. Some of these functional properties are the solubility, hydration, viscosity, coagulation, stabilization, texturing, paste formation, foaming properties, and emulsifying and gelling capacities. Proteins also play an important role in the sensory properties of the food matrices in which they are used, and there is a real synergy between the functional properties and the sensory properties.

The functional properties of proteins, or functionality, are therefore the physical or physicochemical properties which have an effect on the sensory qualities of food systems generated during technological transformations, preservation or domestic culinary preparations.

Whatever the origin of the protein, it is noted that it has an effect on the color, the flavor and/or the texture of a product. These organoleptic characteristics are determining in consumer choice and they are in this case greatly taken into account by manufacturers.

The functionality of proteins is the result of molecular interactions by the latter with their environment (other molecules, pH, temperature, etc.). These properties are generally classed in 3 groups:
 hydration properties which group together the interactions of the protein of water: this covers absorption, retention, wettability, swelling, adherence, dispersion, viscosity, etc., properties,
 structuring properties which group together the properties of protein-protein interaction: this covers precipitation, coagulation, gelling, etc., phenomena,
 surface properties which group together the properties of protein interaction with other polar or nonpolar structures in the liquid or gas phase: this covers emulsifying, foaming, etc., properties.

These various properties are not independent of one another since a functional property can result from several types of interactions or from several functional properties.

The applicant companies have noted that there is a real, unsatisfied need to have a composition having advantageous functional properties, which can be used in the food industry as an at least partial substitute for proteins of animal origin.

In this context, the applicant companies have developed a particular process which makes it possible to obtain a novel composition comprising at least one dairy protein and at least one vegetable protein, having improved functional and/or sensory properties.

SUMMARY OF THE INVENTION

A subject of the present invention is thus a process for obtaining an assembly of at least one vegetable protein and at least one dairy protein, comprising the steps consisting in obtaining a composition comprising at least one vegetable protein, in obtaining a composition comprising at least one dairy protein and in mixing the composition comprising at least one vegetable protein and the composition comprising at least one dairy protein, and in addition one or more identical or different steps of treatment which modifies the conformation of the proteins.

The present invention also relates to an assembly of at least one dairy protein and at least one vegetable protein that can be obtained by means of the process described above. This assembly has improved functional and/or sensory properties compared with the functional and/or sensory properties that would be obtained by the simple juxtaposition of these proteins, for example in the dry mixing of the two types of proteins. The assembly of at least one vegetable protein and at least one dairy protein according to the present invention thus makes it possible to obtain a real synergy in terms of the final properties obtained. This means that the properties of each of the proteins used are not just added and accumulated, but they are either improved or new. This synergy is demonstrated in particular in the examples hereinafter.

Finally, the present invention relates to the use of said assembly in various industrial sectors, and more particularly in the food-processing field. The assembly may be used as a functional agent, and preferably for its solubility or as an emulsifier, a foaming agent, a gelling agent, a viscosifying agent, an overrun agent, a water-retaining agent and/or an agent which can react to heat treatment.

DESCRIPTION OF THE FIGURE

FIG. 1 presents the protein losses measured in the sera of various assemblies (PROMILK 852 B+Floculate) of the present invention and also the protein losses obtained for the dairy protein (PROMILK 852 B 4%) alone during rennet coagulation.

DETAILED DESCRIPTION OF THE EMBODIMENTS

Commonly, the term "assembly of proteins" refers to the combining of several proteins together forming a particular three-dimensional structure.

Indeed, proteins are formed from a succession of amino acids. The radical part of the amino acids bears different chemical functions. Thus, there may be interactions between the radicals of the amino acids, typically hydrophobic interactions, hydrogen bonds, ionic bonds and disulfide bridges. The interactions between radicals have the effect of bringing about folding of the proteins on themselves and between them so as to adopt a three-dimensional supramolecular structure. In this, the assembly of proteins differs from the simple mixture: the proteins are not simply physically mixed, but together form a new structure, having for example a particular size, morphology and composition.

The process which is the subject of the present invention comprises the steps consisting in obtaining a composition comprising at least one vegetable protein, in obtaining a composition comprising at least one dairy protein and mixing the composition comprising at least one vegetable protein and the composition comprising at least one dairy protein.

In the present invention, the term "vegetable protein" denotes all the proteins derived from cereals, oleaginous plants, leguminous plants and tuberous plants, and also all the proteins derived from algae and microalgae, used alone or as a mixture, chosen from the same family or from different families.

These vegetable proteins can be used alone or as a mixture, chosen from the same family or from different families.

The terms "algae" and "microalgae" are intended to mean, in the present application, eukaryotic organisms which are devoid of roots, stalks and leaves, but which have chlorophyll and also other pigments that are incidental to oxygen-producing photosynthesis. They are blue, red, yellow, golden and brown, or else green. They represent more than 90% of marine plants and 18% of the plant kingdom, with their 40 000 to 45 000 species. Algae are organisms that are extremely varied both in terms of their size and shape and in terms of their cellular structure. They live in an aquatic or very humid environment. They contain many vitamins and trace elements, and are true concentrates of active agents that are stimulants of and beneficial to health and beauty. They have anti-inflammatory, moisturizing, softening, regenerating, firming and anti-aging properties. They also have "technological" characteristics which make it possible to give a food product texture. Indeed, the additives E400 to E407 are compounds extracted from algae, the thickening, gelling, emulsifying and stabilizing properties of which are used.

Microalgae in the strict sense are microscopic algae. They are undifferentiated single-cell or multicellular photosynthetic microorganisms separated into two polyphyletic groups: eukaryotes and prokaryotes. Since they live in strong aqueous environments, they can have flagellar mobility.

According to one preferential embodiment, the microalgae are chosen from the group made up of *Chlorella*, *Spirulina* and *Odontella*.

According to an even more preferential embodiment, the microalgae of the present invention are derived from the *Chlorella* genus, and preferably from *Chlorella vulgaris, Chlorella pyrenoidosa, Chlorella regularis, Chlorella sorokiniana*, and even more preferentially from *Chlorella vulgaris*.

In the present application, the term "cereals" is intended to mean cultivated plants of the grass family producing edible grains, for instance wheat, oats, rye, barley, maize, sorghum or rice. The cereals are often milled in the form of flour, but are also provided in the form of grains and sometimes in whole-plant form (fodders).

In the present application, the term "tubers" is intended to mean all the storage organs, which are generally underground, which ensure the survival of the plants during the winter season and often their multiplication via the vegetative process. These organs are bulbous owing to the accumulation of storage substances. The organs transformed into tubers can be:
  the root: carrot, parsnip, cassava, konjac,
  the rhizome: potato, Jerusalem artichoke, Japanese artichoke, sweet potato,
  the base of the stalk (more specifically the hypocotyl): kohlrabi, celeriac,
  the root and hypocotyl combination: beetroot, radish.

In the present application, the term "leguminous plants" denotes plants cultivated specifically for their seeds or their fruits rich in fats, from which oil for dietary, energy or industrial use is extracted, for instance rapeseed, groundnut, sunflower, soybean, sesame and the castor oil plant.

For the purposes of the present invention, the term "leguminous plants" is intended to mean any plants belonging to the family Cesalpiniaceae, the family Mimosaceae or the family Papilionaceae, and in particular any plants belonging to the family Papilionaceae, for instance pea, bean, broad bean, horse bean, lentil, alfalfa, clover or lupin.

This definition includes in particular all the plants described in any of the tables contained in the article by R. Hoover et al., 1991 (Hoover R. (1991) "*Composition, structure, functionality and chemical modification of legume starches: a review*" Can. J. Physiol. Pharmacol., 69, pp. 79-92).

According to one preferential embodiment of the present invention, the vegetable protein belongs to the leguminous plant proteins.

In addition, according to one preferential embodiment, the leguminous plant protein is chosen from the group consisting of alfalfa, clover, lupin, pea, bean, broad bean, horse bean and lentil, and mixtures thereof.

More preferably, said leguminous plant protein is chosen from the group consisting of pea, bean, broad bean and horse bean, and mixtures thereof.

Even more preferably, said leguminous plant protein is derived from pea.

The term "pea" is here considered in its broadest sense, and includes in particular:
  all the varieties of "smooth pea" and of "wrinkled pea", and
  all the mutant varieties of "smooth pea" and of "wrinkled pea", irrespective of the uses for which said varieties are generally intended (food for human consumption, animal feed and/or other uses).

In the present application, the term "pea" includes the varieties of pea belonging to the *Pisum* genus and more particularly to the *Sativum* and *Aestivum* species.

Said mutant varieties are in particular those known as "r mutants", "rb mutants", "rug 3 mutants", "rug 4 mutants", "rug 5 mutants" and "lam mutants" as described in the article by C-L Heydley et al., entitled "*Developing novel pea starches*" *Proceedings of the Symposium of the Industrial Biochemistry and Biotechnology Group of the Biochemical Society*, 1996, pp. 77-87.

Even more preferentially, said leguminous plant protein is derived from smooth pea.

Indeed, the pea is the leguminous plant with protein-rich seeds which, since the 1970s, has been most widely developed in Europe and mainly in France, not only as a protein source for animal feed, but also for food for human consumption.

The pea proteins consist, like all leguminous plant proteins, of three main classes of proteins: globulins, albumins and "insoluble" proteins.

The value of pea proteins lies in their good emulsifying capacities, their lack of allergenicity and their low cost, which makes them an economical functional ingredient.

Furthermore, the pea proteins contribute favorably to sustainable development and their carbon impact is very positive. This is because pea cultivation is environmentally friendly and does not require nitrogenous fertilizers, since the pea fixes nitrogen in the air.

According to the present invention, the composition comprising at least one vegetable protein is preferably a composition comprising at least one pea protein.

The composition comprising at least one vegetable protein, in particular a pea protein, may be in the form of a solution, a dispersion or a suspension or in solid form, in particular in powder form.

The composition comprising at least one vegetable protein, in particular one pea protein, used according to the invention may advantageously have a total protein content (N×6.25) of at least 60% by weight of dry product. Preferably, in the context of the present invention, use is made of a composition having a high protein content, of between 70% and 97% by weight of dry product, and preferably between 76% and 95%, even more preferentially between 78% and 88%, and in particular between 78% and 85%. The total protein content is measured by quantitatively determining the soluble nitrogenous fraction contained in the sample according to the Kjeldahl method. The total protein content is then obtained by multiplying the nitrogen content, expressed as percentage by weight of dry product, by the factor 6.25.

In addition, said composition comprising at least one vegetable protein, in particular one pea protein, can have a soluble protein content, expressed according to a test described hereinafter for measuring protein solubility in water, of between 20% and 99%. Preferably, in the context of the present invention, use is made of a composition having a high soluble protein content of between 45% and 90%, even more preferentially between 50% and 80%, and in particular between 55% and 75%.

To determine the soluble protein content, the content of proteins soluble in water of which the pH is adjusted to 7.5+/−0.1 using a solution of HCl or NaOH is measured by means of a method of dispersion of a test specimen of the sample in distilled water, centrifugation and analysis of the supernatant. 200.0 g of distilled water at 20° C.+/−2° C. are placed in a 400 ml beaker, and the whole is stirred magnetically (magnetic bar and rotation at 200 rpm). Exactly 5 g of the sample to be analyzed are added. The mixture is stirred for 30 min, and centrifuged for 15 min at 4000 rpm. The method for determining nitrogen is carried out on the supernatant according to the method previously described.

These compositions comprising at least one vegetable protein, in particular one pea protein, preferably contain more than 50%, more preferentially more than 60%, even more preferentially more than 70%, even more preferentially more than 80%, and in particular more than 90% of proteins of more than 1000 Da. The determination of the molecular weight of the protein can be carried out according to the method described hereinafter. In addition, these compositions comprising at least one vegetable protein, in particular one pea protein, preferably have a molecular weight distribution profile consisting of:
- 1% to 8%, preferably from 1.5% to 4%, and even more preferentially from 1.5% to 3%, of proteins of more than 100 000 Da,
- 20% to 55%, preferably from 25% to 55%, of proteins of more than 15 000 Da and of at most 100 000 Da,
- 15% to 30% of proteins of more than 5000 Da and of at most 15 000 Da,
- and from 25% to 55%, preferably from 25% to 50%, and even more preferentially from 25% to 45% of proteins of at most 5000 Da.

Examples of compositions comprising at least one vegetable protein, in particular one pea protein, according to the invention, and also the details of the method for determining the molecular weights can be found in patent WO 2007/017572.

According to the present invention, the composition comprising at least one vegetable protein, in particular one pea protein, can be chosen from the group consisting of vegetable protein concentrate and of vegetable protein isolate, preferably of pea protein concentrate and of pea protein isolate. The vegetable protein, and in particular pea protein, concentrates and isolates are defined from the viewpoint of their protein content (cf. the review by J. Gueguen from 1983 in *Proceedings of European congress on plant proteins for human food* (3-4) pp 267-304):
- the vegetable protein, and in particular pea protein, concentrates are described as having a total protein content of from 60% to 75% on a dry basis, and
- the vegetable protein, and in particular pea protein, isolates are described as having a total protein content of from 90% to 95% on a dry basis, the protein contents being measured by the Kjeldhal method, the nitrogen content being multiplied by the factor 6.25.

In another embodiment of the present invention, the composition comprising at least one vegetable protein, in particular one pea protein, may also be a "vegetable protein hydrolyzate", preferably "pea protein hydrolyzate". The vegetable protein, and in particular pea protein, hydrolyzates are defined as preparations obtained by enzymatic hydrolysis or chemical hydrolysis, or by both simultaneously or successively, of vegetable proteins, and in particular pea proteins. The protein hydrolyzates comprise a higher proportion of peptides of various sizes and of free amino acids than the original composition. This hydrolysis can have an impact on the solubility of the proteins. The enzymatic and/or chemical hydrolysis is, for example, described in patent application WO 2008/001183. Preferably, the protein hydrolysis is not complete, i.e. does not result in a composition comprising only or essentially amino acids and small peptides (from 2 to 4 amino acids). The preferred hydrolyzates comprise more than 50%, more preferentially more than 60%, even more preferentially more than 70%, even more preferentially more than 80%, and in particular more than 90% of proteins and of polypeptides of more than 500 Da.

The processes for preparing protein hydrolyzates are well known to those skilled in the art and can, for example, comprise the following steps: dispersion of the proteins in water so as to obtain a suspension, and hydrolysis of this suspension by means of the chosen treatment. Most commonly, it will be an enzymatic treatment combining a mixture of various proteases, optionally followed by a heat treatment intended to inactivate the enzymes that are still active. The solution obtained can then be filtered through one or more membranes so as to separate the insoluble compounds, optionally the residual enzyme, and the high-molecular-weight peptides (greater than 10 000 daltons).

In one preferred embodiment, the composition comprising at least one vegetable protein used for obtaining the assembly according to the invention does not contain gluten. This embodiment is advantageous since there are a certain number of individuals who suffer from gluten intolerance.

Gluten is a group of proteins present in cereals, particularly in wheat, but also in rye, barley and oats. For most individuals, gluten is a normal protein which is readily digested by means of the stomach. However, a small section of the population is incapable of digesting gluten. These gluten-intolerant individuals are most generally denoted as suffering from celiac disease (also known as celiac sprue, gluten-intolerant enteropathy or gluten-sensitive enteropathy). This disease appears when there is a chronic reaction against certain protein chains present in some cereals. This reaction brings about the destruction of the intestinal villi of the small intestine, which causes malabsorption of nutrients and other more or less serious disorders. It is a very restricting disease for which, at the current time, there is no curative treatment.

According to one optional embodiment of the invention, the compositions comprising at least one vegetable protein, in particular one pea protein, can undergo a heat treatment at high temperature and for a short time, it being possible for said treatment to be chosen from HTST (High Temperature Short Time) and UHT (Ultra High Temperature) treatments. This treatment advantageously makes it possible to reduce bacteriological risks.

In the present invention, the term "dairy protein" denotes all proteins derived from milk and from milk-derived products.

From a chemical point of view, milk products stand out in two groups: caseins and serum proteins. Caseins represent 80% of the total proteins of milk. Serum proteins, which represent the remaining 20%, are soluble at pH 4.6. Among the serum proteins are principally β-lactoglobulin, α-lactalbumin, bovine serum albumin, immunoglobulins and lactoferrin.

According to one embodiment of the present invention, the composition comprising at least one dairy protein may be a composition comprising at least one milk protein retentate.

According to another embodiment of the present invention, the composition comprising at least one dairy protein may be a composition comprising at least one casein.

According to another embodiment of the present invention, the composition comprising at least one dairy protein may be a composition comprising at least one serum protein.

According to another embodiment of the present invention, the composition comprising at least one dairy protein may be a composition comprising at least one casein and one serum protein.

The composition comprising at least one dairy protein may be in liquid form or in solid form, in particular in powder form.

The composition comprising at least one dairy protein may in particular be milk or a dairy product.

In legal terms, only one clear definition, dating from 1909, exists defining milk of animal origin: "milk is the integral product of the complete and uninterrupted milking of a healthy well-nourished milking female which is not overworked. It should be collected cleanly and not contain cholesterol."

The name "milk" without any indication of the animal species from which it comes is, from the point of view of French legislation, reserved for cows' milk. Any milk which comes from a milking female other than a cow should be denoted by the name "milk" followed by the indication of the animal species from which it comes, for example "goats' milk", "ewes' milk", "asses' milk", "buffalo milk", etc. However, for the purposes of the present invention, the milk and the dairy products may come from any animal species.

For the purposes of the present invention, the term "dairy product" is intended to mean any product obtained following any treatment of milk, which may contain food additives and other ingredients functionally required for the treatment (definition in the CODEX Alimentarius).

It is known practice to dehydrate liquid milk in order to obtain powder. The composition comprising at least one dairy protein may also be powdered milk, irrespective of the animal origin and the type of the milk.

The composition comprising at least one dairy protein may in particular be chosen from the group made up of wheys and/or buttermilks and/or milk or whey permeates and/or retentates.

Whey, also called milk serum, is the liquid part resulting from the coagulation of milk. Two sorts of wheys are distinguished: those resulting from acid productions of caseins and of fresh cheeses (acid whey), and those resulting from productions of rennet caseins and cooked or semi-cooked pressed cheeses (sweet whey). Whey is generally sold in powder form. Other than water, whey contains lactose (from 70% to 75%), soluble proteins (from 10% to 13%), vitamins (thiamine-B1, riboflavin-B2 and pyridoxine-B6) and minerals (essentially calcium).

Buttermilk, or "churned milk", is conventionally derived from fresh or fermented milk after the production of butter by churning. It is also produced directly from fresh milk by adding ferments. Buttermilk may be in liquid, concentrated or powdered form.

In addition, the dairy proteins can be extracted from milk or from dairy products by means of processes well known to those skilled in the art. These extracted proteins may be commercially available in various forms, for example in powder or liquid form, at various concentrations.

The composition comprising at least one dairy protein may be chosen from the group made up of:
  protein compositions which can be obtained by filtration of milk, in particular protein concentrates or isolates;
  protein coprecipitates which can be obtained by heat treatment and coprecipitation of serum proteins with caseins;
  serum protein compositions, in particular serum protein concentrates or serum protein isolates;

caseins and caseinates, in particular native caseins, acid caseins, rennet caseins, sodium caseinates, potassium caseinates and calcium caseinates;

hydrolyzates of proteins mentioned above;

used alone or in combination with other dairy products such as demineralized whey, milk permeates or whey permeates.

In a first particular embodiment, the composition comprising at least one vegetable protein is a composition comprising a vegetable protein belonging to the leguminous plant proteins, the leguminous plant protein preferably being chosen from the group consisting of alfalfa, clover, lupin, pea, bean, broad bean, horse bean and lentil, and mixtures thereof, and the composition comprising at least one dairy protein is a composition comprising at least one milk protein retentate. According to this particular embodiment, the protein concentration of the assembly is between 70% and 90% by dry weight, and more particularly between 78% and 85% by dry weight.

In a second particular embodiment, the composition comprising at least one vegetable protein is a composition comprising a vegetable protein belonging to the leguminous plant proteins, the leguminous plant protein preferably being chosen from the group consisting of alfalfa, clover, lupin, pea, bean, broad bean, horse bean and lentil, and mixtures thereof, and the composition comprising at least one dairy protein is a composition comprising at least one casein.

Preferably, the composition comprising at least one vegetable protein is a composition comprising a pea protein, in particular a smooth pea protein, and the composition comprising at least one dairy protein is a composition comprising at least one casein, in particular a micellar casein retentate.

According to one preferred embodiment, the composition comprising at least one dairy protein is a total protein concentrate or a total protein isolate.

According to another preferred embodiment, the composition comprising at least one dairy protein is chosen from the group made up of native caseins, acid caseins, rennet caseins, sodium caseinates, potassium caseinates and calcium caseinates.

The dairy protein concentrates are described as having a total protein content greater than the material of origin.

The dairy protein isolates are described as having a total protein content greater than the material of origin and of at least 85% on a dry basis. In the previous definitions, the protein contents are measured using the Kjeldhal method, the nitrogen content being multiplied by the factor 6.38 (conversion factor used for dairy proteins).

The whey proteins are generally obtained by means of ultrafiltration, concentration and drying processes.

The caseins are obtained from skim milk and are precipitated either by acidification by means of acid or of harmless bacterial cultures suitable for food for human consumption (acid caseins), or by addition of rennet or of other milk-coagulating enzymes (rennet caseins). The caseinates are the products obtained by drying acid caseins treated with neutralizing agents. According to the neutralizing agents used, sodium, potassium, calcium and mixed (=co-neutralization) caseinates are obtained. The native caseins can be obtained from skim milk by tangential microfiltration and diafiltration with water.

The dairy protein hydrolyzates are defined as preparations obtained by enzymatic or chemical hydrolysis, or by both simultaneously or successively, of dairy proteins.

The compositions comprising at least one dairy protein extracted from milk or dairy products by means of processes well known to those skilled in the art have different total protein contents.

When the compositions are in the powder form, the protein contents are often expressed as a percentage, i.e. by weight of proteins relative to the weight of powder; the term weight percentage is then used.

Thus, it is known that a powdered milk contains approximately 34% by weight of proteins, that is to say that, in 100 g of milk powder, there are 34 g of proteins.

It is also known that a powdered whey contains between 10% and 15% by weight of proteins, and more precisely around 13% by weight.

In the case of protein isolates, the percentage of proteins in the powder can also be expressed as percentage relative to solids. Thus, a powdered milk isolate containing 85% of proteins relative to solids is the same isolate as that which contains 80.75% by weight of protein if the powder contains a moisture content of 5% (85%×95/100).

According to one optional embodiment of the invention, the compositions comprising at least one dairy protein previously described may also undergo a heat treatment. The treatment of foods with heat (or heat treatment) is today the most important long-term preservation technique. Its objective is to totally or partially destroy or inhibit the enzymes and the microorganisms, the presence or the proliferation of which might spoil the food product under consideration or make it unfit for consumption.

The effect of a heat treatment is linked to the time/temperature pair. Generally, the higher the temperature and the longer the time, the greater the effect. Depending on the effect desired, several heat treatments can be distinguished.

Heat-sterilization consists in exposing the foods to a temperature, generally greater than 100° C., for a period of time sufficient to inhibit the enzymes and any form of microorganisms, even sporulating bacteria. When the sterilization is carried out at high temperature (135° C. to 150° C.) for a period of time not exceeding 15 seconds, the term UHT (Ultra High Temperature) sterilization is used. This technique has the advantage of preserving the nutritional and organoleptic quality of the sterilized product.

Pasteurization is a moderate and sufficient heat treatment which makes it possible to destroy pathogenic microorganisms and a large number of spoilage microorganisms. The temperature of the treatment is generally less than 100° C. and the time is a few seconds to a few minutes. When the pasteurization is carried out at a minimum of 72° C. for 15 seconds, the term HTST (High Temperature Short Time) pasteurization is used. The pasteurization destroys the pathogenic microorganisms and most of the saprophytic flora. However, since not all microorganisms are eliminated by pasteurization, this heat treatment must be followed by abrupt cooling. The pasteurized foods are then usually stored in the cold (+4° C.) in order to slow down the development of the microorganisms still present and the shelf life is usually limited to one week.

Thermization is a heat treatment consisting in bringing the solution to a temperature greater than 40° C. and less than 72° C. It is a lesser form of pasteurization. Its main objective is to reduce the total flora of the milk, without however modifying its technological characteristics.

According to the present invention, said heat treatment may be chosen from the treatments prelisted above.

The mixing of the composition comprising at least one vegetable protein and the composition comprising at least one dairy protein can be carried out according to the methods known to those skilled in the art.

According to a first embodiment, the composition comprising at least one vegetable protein and the composition comprising at least one dairy protein are in liquid form, the solvent preferably being water. The mixture can optionally be diluted or concentrated.

According to a second embodiment, one of the two compositions is in liquid form, the solvent preferably being water, and the other is in powder form. The mixing may consist in introducing the powdered composition into the liquid composition.

According to a third embodiment, both compositions are in powder form. The mixing can consist in mixing the powders in dry form, then optionally in introducing them into water, or in introducing either composition or both compositions in powder form into water, then in mixing them.

The mixing of the two compositions may be advantageously followed by stirring, so as to homogenize the mixture. This may, for example, be mechanical or magnetic stirring. This stirring may be carried out at a temperature of between 1° C. and 100° C., more preferentially between 2° C. and 40° C., and even more preferentially between 4° C. and 35° C.

Preferably, the (weight of nitrogenous matter provided by the composition comprising at least one vegetable protein) to (weight of nitrogenous matter provided by the composition comprising at least one dairy protein) ratio is between 99:1 and 1:99, more preferentially between 80:20 and 20:80, even more preferentially between 63:35 and 35:65.

In the preceding ratio, the respective weights of total proteins are measured using the method in which the soluble nitrogenous fraction contained in the sample is quantitatively determined according to the Kjeldhal method. The total protein content is then obtained by multiplying the nitrogen content, expressed as percentage by weight of dry product, by the factor 6.25. This method is well known to those skilled in the art.

Preferably, the aqueous composition obtained after mixing has a total protein content of between 20% and 100% by weight of dry product, more preferentially between 30% and 100%, and even more preferentially between 40% and 100%.

According to a first preferential embodiment of the present invention, the mixture obtained and containing the composition comprising at least one vegetable protein and the composition comprising at least one dairy protein undergoes a resting phase, during which no treatment is applied. This resting phase can last from a few minutes to several hours. When the duration does not exceed one hour, the term resting phase per se is used. When it is several hours, the term storage phase or waiting phase is then used.

This resting phase makes it possible to stabilize the mixture obtained and containing the composition comprising at least one vegetable protein and the composition comprising at least one dairy protein. The term equilibration phase may also be used without implying a distinction in the present invention.

The process according to the invention also comprises a step of treatment which modifies the conformation of the proteins. In the present invention, the expression "treatment which modifies the conformation of the proteins" denotes any treatment applied to an aqueous composition comprising proteins which has the effect of modifying the primary, secondary, tertiary and/or quaternary structure of these proteins.

The structure of the proteins is the amino acid composition and the three-dimensional conformation of the proteins. It describes the relative position of the various atoms which make up a given protein.

Proteins are made up of a linear series of amino acids bonded by peptide bonds. This series has a three-dimensional organization (or folding) which is specific thereto. From the sequence to the folding, there are 4 levels of structuring of the protein.

The primary structure, or sequence, of a protein corresponds to the linear succession of the amino acids (or residues) which configure it, without reference to a spatial configuration. The proteins are therefore amino acid polymers. Concretely, this primary structure is represented by a succession of letters corresponding to the 20 existing amino acids.

The secondary structure describes the local folding of the main chain of a protein. The existence of secondary structures comes from the fact that the favorable energetic foldings of the peptide chain are limited and that only certain conformations are possible. Thus, a protein may be described by an amino acid sequence, but also by a series of secondary structural elements. Furthermore, certain conformations are clearly favored since they are stabilized by hydrogen bonds between the amide (—NH) and carbonyl (—CO) groups of the peptide backbone. There are three main categories of secondary structures according to the hydrogen bond scaffold, and therefore according to the peptide bond folding: helices, sheets and turns. There are experimental methods for determining the secondary structure, such as nuclear magnetic resonance, circular dichroism or certain infrared spectroscopy methods.

The tertiary structure of a protein corresponds to the folding of the polypeptide chain in space. The term three-dimensional structure is more commonly used. The three-dimensional structure of protein is intimately linked to its function: when the structure is broken by the use of a denaturing agent, the protein loses its function: it is denatured. The tertiary structure of a protein depends on its primary structure, but also on its environment. The local conditions which exist outside each cell compartment, the solvent, the ionic strength, the viscosity and the concentration, contribute to modifying the conformation. Thus, a protein which is soluble in water will need an aqueous environment in order to adopt its three-dimensional structure.

Finally, the quaternary structure of proteins groups together the association of at least two identical or different polypeptide chains via noncovalent bonds, "weak" bonds (H bonds, ionic bonds, hydrophobic interactions and Van der Waals forces), but rarely via disulfide bridges which have the role of creating interchain bonds.

Proteins have a major role in the organoleptic qualities of many fresh or manufactured foods, for instance the consistency and texture of meat and meat products, of milk and derivatives, of pasta and of bread. These food qualities very frequently depend on the structure and the physiochemical properties of the protein constituents or quite simply on the functional properties of the proteins.

The term "functional property" applied to food ingredients is defined as any non-nutritional property which influences the utility of an ingredient in a food. The various properties will contribute so as to result in the desired characteristics of the food. Some of the functional properties of proteins are: solubility, hydration, viscosity, coagulation, texturing, paste formation, and emulsifying and foaming properties.

The conformation of a protein is linked to the secondary and tertiary structure; it is produced by means of low-energy and therefore fragile bonds.

Various protein transformation states exist, depending on the treatment chosen:
- protein denaturation corresponds to the change from an organized state to a disorganized state without rupture of covalent bonds: this is unfolding of the protein;
- polymerization corresponds to aggregate formation;
- precipitation corresponds to the formation of large aggregates with total loss of solubility;
- flocculation corresponds to a non-organized aggregation in the absence of denaturation;
- coagulation results from a protein-protein aggregation with denaturation phenomenon;
- gelling corresponds to an organized aggregation of more or less denatured molecules. There is formation of a continuous three-dimensional network where the polymers interact with one another and with the solvent. It is also the result of the equilibrium which exists between cohesive force and repulsive force.

Denaturation results from a modification of the quaternary, tertiary and secondary structures without fragmentation of the peptide chain. Protein denaturation involves ephemeral structures which can result in total unfolding of the molecule, but it is also considered that denaturation can result from an increase in structure beyond the native form. The unfolding analogous to a random ball structure increases the stability of the molecules. This denaturation modifies the properties of proteins:
- decrease in solubility by unmasking of hydrophobic groups,
- decrease in hydration properties by modification of the water-retaining capacity,
- loss of biological activity,
- increase in susceptibility to proteolysis,
- increase in intrinsic viscosity,
- modification of crystallization or inability to crystallize.

Protein structure is very sensitive to physicochemical treatments. Many processes can result in protein denaturation by affecting the secondary, tertiary and quaternary structures. The physical treatments which can induce denaturation are heating, cooling, mechanical treatments, hydrostatic pressure and ionizing radiation. Interactions with certain chemical products can also denature proteins: acids and bases, metals and high saline concentrations, organic solvents, etc.

The treatment which modifies the conformation of the proteins can be chosen from the group made up of a chemical treatment, a mechanical treatment, a heat treatment, an enzymatic treatment and the combination of several of these treatments.

Among the chemical treatments, mention may in particular be made of treatments which modify the pH of the aqueous composition comprising proteins and treatments which modify the ionic strength of the aqueous composition comprising proteins. Many factors may be involved in chemical denaturing treatments. Firstly, mention may be made of extreme pHs which lead to unfolding of the molecule due to ionization of the latter and a phenomenon of repulsion of the peptide fragments revealed. The loss of ions associated with a protein leads to molecule denaturation. Organic solvents modify the dielectric constant of the medium and, consequently, will modify the distribution of the charges and therefore of the electrostatic forces which maintain the cohesion of the protein structure. Nonpolar solvents can react with the hydrophobic zones and can break the hydrophobic interaction which maintains the conformation of the protein. Finally, chaotropic agents and surfactants, by breaking either hydrogen bonds or hydrophobic interactions, cause protein denaturation.

Among the mechanical treatments, also called physical treatments, mention may in particular be made of treatments in which the aqueous composition comprising proteins is subjected to high-pressure homogenization.

Among the heat treatments, mention may in particular be made of treatments in which the aqueous composition comprising proteins is heated. The heat treatments are capable of modifying the functionalities of most ingredients. There is a large variety of possible "heat treatments" since the latter are governed by the definition of the time-temperature pair.

The heat treatment may generate profound modification, for instance the destruction of sulfur-containing amino acids with the production of $H_2S$, of dimethyl sulfide, of cysteic acid (in the case of dairy proteins, meat proteins, fish meat proteins, etc.), the destruction of serine, of threonine and of lysine. Deamination reactions may occur if the temperature is greater than 100° C. Ammonia comes from the "acetamido" groups of glutamine and of asparagine; while there is modification of the functional properties (modification of the isoelectric point (pI), appearance of new covalent bonds), there is no modification of the nutritional value.

Among the enzymatic treatments, mention may in particular be made of controlled hydrolysis and crosslinking. The enzymatic modification of proteins constitutes a powerful tool for improving the technological properties of these macromolecules. Hydrolysis using proteases is a well-known method for improving protein solubility. Generally, it is observed that the solubility increases with the degree of hydrolysis, but depends on the enzymes used, the specificity of which determines the size and the sequence of the peptides released. The ability of the peptides to form and to stabilize foams and emulsions also depends on the physicochemical characteristics. These peptides must have an amphiphilicity and have a minimum size (>15-20 residues) in order to form and stabilize the interfacial layer. However, weaker foaming properties are quite often observed. On the other hand, controlled hydrolysis can promote the production of emulsifying polypeptides, the functionality of which is greater than that of the property of origin.

Unlike proteases, other enzymes appear to be particularly advantageous for modifying the functional properties of proteins. Among these, transglutaminases have proven to be very effective. Transglutaminases are transferases which catalyze the formation of a*(*-glutamyl)amine bond between the carboxyamide group of a glutaminyl residue of a protein and a primary amine group. If this function is the amino group of the lysyl residue, there is formation of an isopeptide bond and protein crosslinking. In the absence of an available amine in the medium, water can play the role of acyl acceptor and the carboxamide group is then deamidated. Thus, transglutaminases can induce protein crosslinking and can enable gelling.

The treatment which modifies the conformation of the proteins can be applied to the composition comprising at least one vegetable protein, to the composition comprising at least one dairy protein or to the composition obtained after mixing these two compositions.

The process for obtaining the assembly according to the invention may comprise a single step of treatment which modifies the conformation of the proteins, it being possible for this treatment step to be applied to one of the two protein compositions before mixing or to the composition obtained after mixing these two compositions.

Alternatively, the process for obtaining the assembly according to the invention may comprise several steps of treatment which modifies the conformation of the proteins, it being possible for the treatments to be optionally of the same nature, and to be applied to different compositions or successively to the same composition.

According to a first advantageous embodiment of the present invention, the step of treatment which modifies the conformation of the proteins consists in lowering the pH of the composition comprising at least one vegetable protein to a value less than or equal to 4, before the mixing with the composition comprising at least one dairy protein. Preferably, the pH is lowered to a value less than or equal to 3, even more preferentially less than or equal to 2.5, in particular between 2 and 2.5.

This pH-lowering step can be carried out by adding an acid to the aqueous vegetable composition, and preferably an acid of which the use is authorized in the food-processing field. The acid may, for example, be chosen from the group consisting of hydrochloric acid, acetic acid, phosphoric acid, citric acid, sorbic acid, benzoic acid, tartaric acid, lactic acid, propionoic acid, boric acid, malic acid and fumaric acid. The addition of the acid may optionally be accompanied by stirring of the aqueous composition.

The acidified composition may optionally be stirred for a period of at least 15 minutes, more preferentially of at least 30 minutes, even more preferentially of at least 1 hour and in particular of at least 2 hours. This stirring advantageously promotes the dissociation and the solubilization of the vegetable proteins in the acidified composition. This stirring step can be carried out at a temperature which promotes the dissociation and the solubilization, preferably between 1° C. and 100° C., more preferentially between 2° C. and 40° C., and even more preferentially between 4° C. and 35° C.

According to a second advantageous embodiment of the present invention, the step of treatment which modifies the conformation of the proteins consists in lowering the pH of the composition comprising at least one dairy protein to a value less than or equal to 4, before the mixing with the composition comprising at least one vegetable protein. This step can be carried out as described above for the composition comprising at least one vegetable protein.

Advantageously, this second embodiment may be combined with the first embodiment, it therefore being possible for the process to comprise two steps of treatment which modifies the conformation of the proteins, one applied to the composition comprising at least one vegetable protein, the other applied to the composition comprising at least one dairy protein, the two treatments consisting in lowering the pH of the composition to a value less than or equal to 4.

When the process according to the invention comprises a step of treatment which consists in lowering the pH of the composition, it may advantageously also comprise a step of raising the pH of the composition obtained after mixing to a value between 5 and 8. Preferably, the pH is raised to a value between 5.5 and 7.5, even more preferentially to a value between 6 and 7.

This pH-raising step may be carried out by adding an alkali to the mixture, preferably an alkali of which the use is authorized in the food-processing field. The base may, for example, be chosen from the group consisting of sodium hydroxide, sodium sorbate, potassium sorbate, calcium sorbate, sodium benzoate, potassium benzoate, sodium formate, calcium formate, sodium nitrate, potassium nitrate, potassium acetate, potassium diacetate, calcium acetate, ammonium acetate, sodium propionate, calcium propionate and potassium propionate. The addition of the base may optionally be accompanied by stirring of the mixture, for a period of at least 15 minutes, more preferentially of at least 30 minutes, even more preferentially of at least 1 hour and in particular of at least 2 hours.

This stirring step may be carried out at a temperature which promotes the dissociation and the solubilization, preferably between 1° C. and 100° C., more preferentially between 2° C. and 40° C., and even more preferentially between 4° C. and 35° C.

According to a third advantageous embodiment of the present invention, the step of treatment which modifies the conformation of the proteins consists of a step of homogenization of the composition obtained after mixing. It was noted that this homogenization step advantageously made it possible to obtain a better solubilization of the vegetable proteins and to promote the interactions between the vegetable proteins and the dairy proteins.

The homogenization can be carried out according to techniques known to those skilled in the art. A particularly preferred technique is high-pressure homogenization. It is a physical treatment during which a liquid or pasty product is projected under strong pressure through a homogenization head of specific geometry. This treatment results in a reduction in the size of the solid or liquid particles which are in dispersed form in the treated product. The pressure of the high-pressure homogenization is typically between 30 bar and 1000 bar. In the process which is the subject of the present invention, this pressure is preferably between 150 bar and 500 bar, more preferentially between 200 bar and 400 bar, and even more preferentially between 250 bar and 350 bar. In addition, one or more homogenization cycles may be carried out. Preferably, the number of high-pressure homogenization cycles is between 1 and 4.

The homogenization may also be carried out using other known devices, for example chosen from mixers, colloid mills, microbead mill homogenizers, ultrasonic homogenizers and valve homogenizers.

The process for producing the assembly according to the invention may comprise several steps of homogenization of the composition obtained after mixing. In particular, a first homogenization step may be applied to the composition obtained after mixing which has undergone, beforehand, a treatment step consisting in lowering the pH of the composition, then a second homogenization step may be applied to the composition after a step of raising the pH.

Advantageously, this third embodiment may be combined with the first or second embodiment, it therefore being possible for the process to comprise two steps of treatment which modifies the conformation of the proteins, one applied to the composition comprising at least one vegetable protein or to the composition comprising at least one dairy protein, consisting in lowering the pH of the composition to a value less than or equal to 4, and the other consisting in homogenizing the composition obtained after mixing.

In particular, the process for obtaining an assembly of at least one vegetable protein and at least one dairy protein may comprise the steps consisting in:
  obtaining an aqueous composition comprising at least one vegetable protein;
  lowering the pH of said composition to a value less than or equal to 4 so as to obtain an acidified composition;
  introducing at least one dairy protein into said acidified composition so as to obtain a mixture;
  homogenizing the mixture obtained;

raising the pH of said homogenized mixture to a value between 5 and 8 so as to obtain said assembly.

The process which is the subject of the present invention makes it possible to obtain an aqueous composition comprising an assembly of at least one vegetable protein and at least one dairy protein, which is also a subject of the present invention.

It has in fact been noted that the preparation process described above, and in particular the presence of a step of treatment which modifies the conformation of the proteins, promotes the formation of assemblies between the vegetable protein and the dairy protein.

The assembly of at least one vegetable protein and at least one dairy protein thus obtained, which is also a subject of the present invention, differs from the simple physical mixture of these two types of proteins. It involves a new structure on a supramolecular scale.

Said assembly may be in the form of an aqueous composition, of a concentrated aqueous composition or of a powder. In the case of an aqueous composition, the term aqueous dispersion is instead used.

An aqueous composition, or aqueous dispersion, comprising the assembly of at least one vegetable protein and at least one dairy protein is obtained at the end of the process which is the subject of the present invention. This aqueous composition or dispersion has a pH preferably of between 5 and 8, more preferentially between 5.5 and 7.5, and even more preferentially between 5.8 and 7.1.

The total protein content of the composition is preferably between 20% and 100% by weight of dry product, more preferentially between 30% and 90%, even more preferentially between 35% and 85%, and in particular between 40% and 80%.

Said contents are indicated as percentage by weight of product relative to the dry weight of the composition.

According to another embodiment, the protein content of the composition is between 50% and 90% by weight relative to dry product.

When there is an aqueous dispersion, i.e. when the assembly is suspended in a liquid, the protein content is indicated as concentration by weight, i.e. as a weight concentration which expresses the ratio between the weight of a solute, i.e. the proteins, and the volume of aqueous dispersion.

Said assembly comprising at least one vegetable protein and at least one dairy protein may optionally comprise other ingredients. These optional ingredients may have properties which are advantageous for certain applications. They may be chosen from the group made of soluble fibers, insoluble fibers, vitamins, mineral salts, trace elements, and mixtures thereof. The optional ingredients may be provided by the compositions comprising at least one vegetable protein or at least one dairy protein, or they may be added during the preparation of the assembly.

According to one preferential embodiment of the present invention, said assembly comprising at least one vegetable protein and at least one dairy protein includes a soluble vegetable fiber.

Preferably, said soluble fiber of vegetable origin is chosen from the group made up of fructans, including fructooligosaccharides (FOSs) and inulin, glucooligosaccharides (GOSs), isomaltooligosaccharides (IMOs), trans-galactooligosaccharides (TOSs), pyrodextrins, polydextrose, branched maltodextrins, indigestible dextrins and soluble oligosaccharides derived from oleaginous or protein-producing plants.

The term "soluble fiber" is intended to mean fibers that are soluble in water. The fibers can be assayed according to various AOAC methods. By way of example, mention may be made of AOAC methods 997.08 and 999.03 for fructans, FOSs and inulin, AOAC method 2000.11 for polydextrose, AOAC method 2001.03 for assaying the fibers contained in branched maltodextrins and indigestible maltodextrins, or AOAC method 2001.02 for GOSs and also soluble oligosaccharides derived from oleaginous or protein-producing plants.

According to one particularly advantageous embodiment of the present invention, said assembly comprises soluble vegetable fibers which are branched maltodextrins.

The term "branched maltodextrins" (BMDs) is intended to mean the specific maltodextrins identical to those described in patent EP 1 006 128-B1 of which the applicant is the proprietor. These BMDs have the advantage of representing a source of indigestible fibers beneficial to the metabolism and to the intestinal equilibrium. In particular, use may be made of BMDs having between 15% and 35% of 1-6 glucosidic bonds, a reducing sugar content of less than 20%, a weight-average molecular weight Mw of between 4000 and 6000 g/mol and a number-average molecular weight Mn of between 250 and 4500 g/mol.

Certain subfamilies of BMDs described in the abovementioned application can also be used in accordance with the invention. They are, for example, high-molecular-weight BMDs having a reducing sugar content at most equal to 5 and an Mn of between 2000 and 4500 g/mol. Low-molecular-weight BMDs having a reducing sugar content of between 5% and 20% and a molecular weight Mn of less than 2000 g/mol can also be used.

The use of Nutriose®, which is an entire range of soluble fibers, recognized for their benefits, and produced and sold by the applicant, is particularly advantageous. The products of the Nutriose® range are partially hydrolyzed wheat starch or corn starch derivatives which contain up to 85% total fiber. This richness in fiber makes it possible to increase the digestive tolerance, to improve calorie control, to prolong energy release and to obtain a lower sugar content. In addition, the Nutriose® range is one of the most well-tolerated fiber compositions available on the market. It shows higher digestive tolerance, allowing better incorporation than other fibers, thereby representing real dietary advantages.

According to one embodiment of the invention, the process for obtaining said assembly also comprises a step consisting in subjecting the aqueous composition comprising an assembly of at least one vegetable protein and at least one dairy protein to a heat treatment at high temperature and for a short time, it being possible for said treatment to be chosen from HTST (High Temperature Short Time) and UHT (Ultra High Temperature) treatments. This optional step advantageously makes it possible to reduce the risks of bacteriological contamination and to improve the storage properties of the composition.

The aqueous composition comprising the assembly according to the present invention may optionally be concentrated. The process which is the subject of the invention may therefore also comprise a step of concentration of said composition. This concentration step may optionally take place after a heat treatment step and/or a stabilization step.

After concentration, the total protein content of the concentrated composition is preferably between 100 g/kg and 600 g/kg by weight of proteins relative to the total weight of the composition, more preferentially between 150 g/kg and 400 g/kg and in particular between 200 g/kg and 300 g/kg.

The process which is the subject of the invention may also comprise a step consisting in drying the optionally concentrated aqueous composition comprising the assembly of at least one vegetable protein and at least one dairy protein.

The drying process may be chosen from the techniques known to those skilled in the art, and in particular from the group made up of spray-drying, extrusion and lyophilization, granulation, fluidized bed, vacuum rolls, and micronization.

The operating conditions of the drying step are adapted to the selected equipment, so as to enable a powder to be obtained.

Spray-drying is a unit drying operation which consists in converting into a powder a liquid sprayed in the form of droplets brought into contact with a hot gas. The spraying conditions determine the size of the droplets produced, their path, their speed and, consequently, the final size of the dry particles, and also the properties of the powders obtained: flow, instant nature related to their solubility, density, compressibility, friability, etc. The spray-drying step can be carried out in a spray drier or a spray-drying tower, in which the liquid composition to be dried is sprayed in a stream of hot gas. This hot gas provides the heat necessary for evaporating the solvent of the composition and absorbs, in order to evacuate it, the moisture released by the product during drying. The liquid composition is introduced at the top via a nozzle or a turbine, and the "spray-dried" powder obtained is harvested at the bottom of the tower. The dry solid is separated from the spray-drying gas by means of one (or more) cyclone(s), or by filtration (sleeve filter, for example). In certain cases, if this is found to be necessary, the tower can be filled with an inert gas in order to prevent oxidation phenomena.

Extrusion is a process in which a material is forced to pass through a die having the cross section of the part to be obtained. The temperature parameters are easily selected by those skilled in the art according to the water content of the composition before drying. The extruded composition can then be successively subjected to cooling, to milling and, optionally, to sieving in order to obtain a powder.

Lyophilization, or cryodessication, consists in removing the water from the composition by subjecting said composition to a deep-freezing phase, then to a phase of heating at very low pressure in order to cause sublimation of the solvent of the composition.

The assembly of at least one vegetable protein and at least one dairy protein according to the invention may be in the form of a powder.

The mean size of the powder obtained can be characterized by its volume mean diameter (arithmetic mean) D4,3, also known as laser volume mean diameter D4,3. It is preferably between 10 μm and 500 μm, preferably between 30 μm and 350 μm and even more preferentially between 50 μm and 200 μm.

According to one preferential embodiment, the volume mean diameter D4,3 of said granulated powder is between 60 μm and 120 μm.

According to one particular embodiment of the present invention, 90% of the powder has a diameter less than 1000 μm, preferably less than 500 μm, and even more preferentially less than 400 μm. In particular, 90% of the powder has a diameter less than 370 μm. This value corresponds to the $d_{90}$.

According to another particular embodiment of the present invention, 50% of the powder has a diameter less than 500 μm, preferably less than 300 μm, and even more preferentially less than 250 μm. In particular 50% of the powder has a diameter less than 220 μm. This value corresponds to the $d_{50}$.

According to another particular embodiment of the present invention, 10% of the powder has a diameter less than 300 μm, preferably less than 200 μm, and even more preferentially less than 150 μm. In particular, 10% of the powder has a diameter less than 100 μm. This value corresponds to the $d_{10}$.

These particle size measurements, in particular the volume mean diameter D4,3 and the three values $d_{90}$, $d_{50}$, and $d_{10}$, are determined on an LS 230 Laser diffraction particle size analyzer from the company Beckman-Coulter, equipped with its powder dispersion module (dry process), according to the technical manual and the specifications of the constructor. The measuring range of the LS 230 Laser diffraction particle size analyzer is from 1 μm to 2000 μm.

The assembly which is the subject of the present invention has functional and/or sensory properties which are different from those of the simple physical mixture of vegetable proteins and dairy proteins. In particular, this assembly has at least one of the following functional properties:

an improved solubility;
an improvement in the holding in suspension;
an improved coagulating capacity;

compared with the simple physical mixture of vegetable proteins and dairy proteins. A synergistic effect on the functional properties is consequently observed with the assembly according to the invention.

In addition, the assembly according to the invention may have advantageous functional properties, in particular:

an emulsifying capacity;
a foaming capacity;
a gelling capacity;
a thickening capacity;
a viscosifying capacity;
an overrun capacity;
a wetting capacity (water absorption capacity);
a film-forming and/or adhesive capacity;
a thermal reactivity capacity;
a capacity in Maillard reactions.

A link exists between the functional properties and the sensory properties. The synergy demonstrated on the functional properties is therefore also found on the sensory properties of the assembly according to the invention.

Synergy commonly reflects a phenomenon via which several participants, factors or influences acting together create an effect that is greater than the sum of the expected effects if they had operated independently, or create an effect that each of them would not have been able to obtain by acting on their own. In the present application, the word is also used to denote a result that is more favorable when several elements of a system act in concert.

In the context of the present invention, the synergy reflects the existence of an intimate mixture between the various constituents of the assembly, the fact that their distribution within the assembly is substantially homogeneous, and the fact that said constituents are not only linked together by a simple physical mixture.

The applicant companies have noted the advantage of a mixture of at least one dairy protein and at least one vegetable protein, the physical characteristics of which have been modified by using an appropriate process, such that very advantageous functional properties, which cannot be obtained if each compound is used separately or if the compounds are used simultaneously but in the form of a simple mixture of the various constituents, are simultaneously obtained.

Very advantageous functional properties conferred by said assembly concern its emulsifying, foaming and gelling capacities, in comparison with the simple mixture of the constituents of this assembly.

The emulsifying properties are due to the ability to reduce interfacial tensions between hydrophilic and hydrophobic constituents of a food. They are directly linked to the solubility of the protein. The powders which have these surface properties will have a considerable potential for use in emulsions in general, in refatted or nonrefatted milk powders, and also in foods containing water and fats (cooked pork meats, meat, condiments).

Thus, one of the advantageous uses of the assembly according to the present invention or which can be obtained according to the implementation of the process for preparing the assembly according to the invention as described above is that it can be used as an emulsifier in the abovementioned compositions, for totally replacing any other emulsifier, and in particular lecithin. Said assembly can itself be totally free of emulsifier, considered to be additives according to European regulations. Moreover, one of the advantageous uses of the assembly according to the present invention or which can be obtained according to the implementation of the process for preparing the assembly according to the invention as described below is that it can be used as an emulsifier in the abovementioned compositions, for totally replacing any other emulsifier, and in particular lecithin.

Indeed, the use of said assembly makes it possible to completely eliminate lecithin from food formulations, and more particularly the food formulations which are totally or partially in the form of an emulsion, i.e. which contain at least two immiscible ingredients (typically water and oil).

Generally, emulsifiers, sometimes called emulsifying agents, stabilize emulsions. The emulsifiers currently used in industries are either purified natural products or synthetic chemical products, the structures of which are very close to those of the natural products.

They are most commonly surfactants or surface agents. They are molecules which possess one end that has an affinity for water (hydrophilic) and one end that has an affinity for oil (hydrophobic). In the food-processing industry, emulsifiers are used to increase the creaminess of certain products, making it possible to obtain a particular texture. One of the most widely known emulsifiers is unquestionably lecithin.

Indeed, lecithin, also known as phosphatidylcholine, is conventionally used as an emulsifier in the food, cosmetics and other industries. It is a natural emulsifier which is made industrially by means of an aqueous treatment of soya oil. It is in the form of a brown-colored pasty liquid. It does not have a very appetizing appearance, nor a very pleasant taste. Lecithin is classified in the lipid category. It can also be extracted from egg yolks, but the process is too expensive to be applied industrially.

Lecithins are food additives and are subject, like the other food additives, to strict European regulation which governs the assessment of their innocuousness, their authorization and their labeling. These regulations require that all added emulsifiers, in whatever form, be mentioned on the packaging of the product, either by virtue of their name or by virtue of their European code (letter E followed by a number, E322 for lecithin) like all the other food additives.

What is more, since lecithins are extracted from soya for use industrially, they have also suffered the repercussions of the negative image conveyed by genetically modified organisms, to which soya can belong.

Thus, the assembly according to the present invention or which can be obtained according to the implementation of the process for preparing the assembly according to the invention as defined above, which is preferably itself devoid of emulsifiers such as lecithin, makes it possible to avoid the use of other emulsifiers, and in particular of lecithin, and thus makes it possible to be free of both the risks of allergies and the negative image associated with soya, and also the labeling, on the packaging, of lecithin as a food additive.

The foaming properties, which are highly appreciated in patisseries (cakes, soufflés, meringues) and in the manufacture of mousses, based on milk or the like, and of whipped creams, are the result of partial unfolding of the proteins which orient themselves at the water/air interface. The assembly has an excellent foaming capacity, which is extremely stable over time.

Another very advantageous property conferred by said assembly according to the present invention is the clear improvement in, on the one hand, the taste and, on the other hand, the palatability and the body, which is also defined by the viscosity in the mouth. Indeed, the assembly has a neutral taste, unlike the simple mixture of the two constituents which are at least one dairy protein and at least one vegetable protein, which can itself have a more marked leguminous plant taste and consequently curb certain food applications. In some applications, the palatability and the body are also improved compared with the simple mixture.

These very advantageous functional properties which are the result of the actual synergy between the constituents of the assembly and which do not exist with simple mixtures mean that they are intended, inter alia, for very diversified and varied applications.

Another aspect of the present invention relates to the use of the assembly of at least one vegetable protein and at least one dairy protein according to the invention in the fields of cosmetics, detergence, agrochemistry, industrial and pharmaceutical formulations, construction materials, drilling fluids, in fermentation, in animal feed and in the food-processing field. The use in the food-processing field is particularly preferred.

Consequently, the present invention also relates to cosmetic, detergent and agrochemical compositions, industrial and pharmaceutical formulations, construction materials, drilling fluids, fermentation media, animal feed compositions and food applications comprising the assembly according to the present invention or which can be obtained according to the implementation of the process which is the subject of the present invention.

In these fields, the assembly according to the invention may be used as a functional agent, and in particular as:

an emulsifier,
a foaming agent,
a gelling agent,
a thickener,
a viscosifying agent,
an overrun agent,
a water-retaining agent,
a film-forming and/or adhesive agent,
an agent which has a capacity in Maillard reactions.

Consequently, the present invention also relates to an emulsifying agent, a foaming agent, a gelling agent, a viscosifying agent, an overrun agent, a water-retaining agent and/or a thermal reagent (i.e. an agent which has a capacity in Maillard reactions), comprising the assembly according to the present invention or which can be obtained by means of the process which is the subject of the present invention.

The invention thus extends in particular to the food formulations comprising the assembly according to the invention which are chosen from the group made up of:
- beverages,
- dairy products (including, for example, fromage frais and ripened cheeses, processed cheeses, optionally processed cheese spreads, fermented milks, milk smoothies, whipped creams, fermented creams, mousses, overrun products, yoghurts, speciality dairy products, ice creams produced from milk),
- milk desserts,
- preparations intended for clinical nutrition and/or for individuals suffering from undernourishment,
- preparations intended for infant nutrition,
- mixtures of powders intended for diet products, or for sportspersons,
- hyperproteinated products for dietetic or specific nutrition,
- soups, sauces and cooking aids,
- confectionary products, for instance chocolate and all the products derived from the latter,
- meat-based products, more particularly in the fine paste and brine sectors, in particular in the production of hams and cooked pork meats,
- fish-based products, such as surimi-based products,
- cereal products such as bread, pasta, cookies, pastries, cereals and bars,
- vegetarian products and ready meals,
- fermented products based on vegetable proteins, for instance tofu,
- whitening agents such as coffee whiteners,
- products intended for feeding animals, for instance products intended for feeding calves.

One of the particularly advantageous and valuable uses of the present invention relates to the production of a dairy product chosen from the group made up of fromage frais and ripened cheeses, cheese spreads, fermented milks, milk smoothies, yoghurts, speciality dairy products, and ice creams produced from milk.

According to another more preferential embodiment, the assembly according to the invention is used for the production of cheeses.

In the present invention, the term "cheese" denotes a food obtained using coagulated milk or dairy products, such as cream, and then optionally draining, possibly followed by a fermentation step and, optionally, by ripening (ripened cheeses). According to French decree No. 2007-628 of Apr. 27, 2007, the name "cheese" is reserved for the fermented or nonfermented, ripened or nonripened product obtained from materials of exclusively dairy origin (whole milk, partially or totally skim milk, cream, fat, buttermilk), used alone or as a mixture, and totally or partially coagulated before draining or after partial elimination of their water.

In the present invention, the term "cheese" also denotes all processed cheeses and all processed cheese spreads. These two types of cheeses are obtained by milling, mixing, melting and emulsification, under the effect of heat and emulsifiers, of one or more varieties of cheese, with or without the addition of dairy constituents and/or of other food products (cream, vinegar, spices, enzymes, etc.).

In another preferential embodiment, the assembly according to the invention is used for the production of yoghurts or fermented milks.

The invention will be even more clearly understood on reading the examples that follow, which are meant to be illustrative, referring only to certain embodiments and to certain advantageous properties according to the invention, and nonlimiting.

EXAMPLES

Example 1

Preparation of the Protein Assemblies

A. Raw Materials

Dairy Proteins:

The dairy proteins used are derived from a milk fraction and contain 92% of micellar caseins relative to the total nitrogenous matter. This batch is called micellar casein retentate Promilk 852 B sold by the company Ingredia, and is in liquid form (retentate containing 15% of solids), stabilized by addition of 0.02% of bronopol (preservative), and stored at 4° C.

Vegetable Proteins:

The examples were carried out with three different batches of pea proteins.

A batch of pea proteins obtained by ultrafiltration referred to as UF. This batch was obtained by passing a liquid extract of Nutralys® S85 M sold by the company Roquette Fréres over a membrane with a cut-off threshold of 50 KD. The purified proteins obtained were concentrated by diafiltration according to the conventional techniques until a concentrated solution containing 75% proteins was obtained. Finally, the protein concentrate was lyophilized and the powder obtained was stored at 4° C.

A powder of Nutralys® S85 M pea protein sold by the company Roquette Fréres having a total protein content of 85%.

A pea protein flocculate obtained by isoelectric precipitation (pH 4.5) of Nutralys® S85 M. The flocculate is undried, but stabilized through the addition of sodium azide at 0.02%.

B. The Processes for Mixing: Forming the Assemblies

The solubilization of the pea proteins is an important step since they are globular proteins that are soluble at extreme pHs (ph≤3 and ≥7). The solubilization of these proteins allows them to interact with caseins, and makes it possible to obtain a really intimate mixture, explaining the synergy observed in the functional properties.

For the various assemblies prepared between the pea proteins and the dairy proteins, the final protein content of the protein assemblies is 4%, i.e. 40 mg/ml of total proteins in the assembly.

Three Assembly Strategies were Tested a. Strategy for Assembly at pH 7

Preparation of a solution of 16 mg/ml of pea protein powder in water. No pH modification is required. The pH obtained is 6.9-7. Stirring at 500 rpm with a magnetic bar for 2 h.

Preparation of a solution of 64 mg/ml of Promilk 852 B dairy protein powders. No pH modification is required. The pH obtained is 7.

50/50 (v/v) mixing of the pea proteins with the dairy proteins.

Stirring at 550 rpm for 1 hour at ambient temperature.

Final pH obtained is 6.9-7.

Homogenization by means of two passes at 300 bar at ambient temperature.

b. Strategy for Assembly while Lowering the pH to 5.8-6
- Preparation of a solution of 16 mg/ml of pea protein powder in water.
- Lowering of the pH to 2.5 with 1N HCl with stirring at 500 rpm.
- Solubilization with stirring at 500 rpm with a magnetic bar at 4° C. for 2 hours.
- Preparation of a solution of 64 mg/ml of Promilk 852 B dairy protein powders. No pH modification is required. The pH obtained is 7.
- Pour the pea protein solution into the dairy protein solution in a 50/50 ratio. The mixing is carried out dropwise with stirring at 1000 rpm under the control of a pH-meter so as not to descend below a pH of 5.3. Depending on the pea protein nature (UF, Nutralys or flocculate), the final pH of the mixture is between 5.8 and 6.
- Homogenization by means of two passes at 300 bar at ambient temperature.

c. Strategy for Assembly while Lowering the pH to 5.8-6, then Raising it to 6.9
- Preparation of a solution of 16 mg/ml of pea protein powder in water.
- Lowering of the pH to 2.5 with 1N HCl with stirring at 500 rpm.
- Solubilization with stirring at 500 rpm with a magnetic bar at 4° C. for 2 hours.
- Preparation of a solution of 64 mg/ml of Promilk 852 B dairy protein powders. No pH modification is required. The pH obtained is 7.
- Pour the pea protein solution into the dairy protein solution in a 50/50 ratio. The mixing is carried out dropwise with stirring at 1000 rpm under the control of a pH-meter so as not to descend below a pH of 5.3. Depending on the pea protein nature (UF, Nutralys or flocculate), the final pH of the mixture is between 5.8 and 6.
- Raising of the pH of the assemblies to 6.9 with 1N sodium hydroxide.
- Homogenization by means of two passes at 300 bar at ambient temperature.

C. Analysis of the Protein Assemblies

In order to be able to carry out the various analyses of, on the one hand, the raw materials and, on the other hand, the assemblies, it was necessary to centrifuge the various samples and to work only on the soluble fraction.
- Centrifugation of the protein solutions and of the assemblies at 15 000 g for 30 min at 20° C.
- Filtration of the supernatant through a cellulose filter with pore openings of 0.45 µm.

Example 2

Protein Content Determination

In order to determine the protein content in the various samples, the assaying of the soluble nitrogenous fraction contained in the sample can be carried out according to the Kjeldahl method (NF V03-050, 1970). The ammoniacal nitrogen determination is based on the formation of a colored complex between the ammonium ion, sodium salicylate and chlorine, the strength of the coloration of which is measured at 660 nm. This method is carried out with a Technicon automatic continuous liquid flow apparatus.

The protein content of the samples is estimated by multiplying their nitrogen content by the conversion factor 6.25.

This method is well known to those skilled in the art.

In order to determine the soluble protein content, the content of soluble proteins in water of which the pH is adjusted to 7.5+/−0.1 using an HCl or NaOH solution is measured by means of a method of dispersion of a test specimen of the sample in distilled water, centrifugation and analysis of the supernatant. 200.0 g of distilled water at 20° C.+/−2° C. are placed in a 400 ml beaker, and the whole thing is placed under magnetic stirring (magnetic bar and rotation at 200 rpm). Exactly 5 g of the sample to be analyzed are added. The mixture is stirred for 30 min, and centrifugation is carried out for 15 min at 4000 rpm. The method for determining the nitrogen content is carried out on the supernatant according to the method previously described.

Example 3

Results of the pH-Lowering Strategy

The objective of the lowering of the pH (2.5) as described in example 1 above is to solubilize the pea proteins in order to change their conformation and to bring about their folding in such a way that their hydrophobic sites are exposed to the solvent and can interact with the dairy proteins.

Table 1 below shows the soluble and insoluble fractions of the pea proteins as a function of the pH.

TABLE 1

| Pea proteins | pH 7 | pH 2.5 raised to 7 |
|---|---|---|
| Total concentration (mg/ml) | 16 | 16 |
| Soluble fraction (mg/ml) | 7.5 | 10.7 |
| Insoluble fraction (mg/ml) | 8.5 | 5.3 |

The assaying of the soluble proteins in the pea protein solutions shows an improvement in the solubility with the lowering of the pH. Indeed, the solution of 16 mg/ml has a soluble fraction of 7.5 mg/ml, at pH 7, whereas up to 10.7 mg/ml are solubilized by lowering the pH to 2.5 and raising it back up to 7.

Example 4

Determination of the Stability of the Protein Assemblies Obtained

The stability of the proteins in the starting raw materials at the various pHs was assessed and then compared to the behavior of these same proteins in the assemblies. This physical stability was evaluated by measuring:
- the maintaining in suspension of the proteins,
- the solubility of the proteins,
- the dispersibility of the proteins.

Each time, the measurements were carried out on the starting raw materials (pea proteins at 8 mg/ml and dairy proteins at 32 mg/ml), and also on the assemblies obtained according to example 1.

A. Measurement of the Maintaining in Suspension of the Proteins

The maintaining in suspension of the protein assemblies and of the raw materials was assessed by monitoring the sedimentation kinetics for 3 hours using a camera. The images taken every minute were analyzed by the software and the values of the levels of gray restored in digital format.

B. Solubility Measurement

The solubility of the proteins in the protein assemblies was compared with the solubility of the proteins in the starting raw materials. In order to measure the solubility, centrifugations were carried out at 5000 g for 10 minutes at 20° C., and the protein concentration was determined in the supernatants.

C. Dispersibility Measurement

The dispersibility of the proteins in the protein assemblies was compared with the dispersibility of the proteins in the starting raw materials. In order to measure the dispersibility, centrifugations were carried out at 300 g for 5 minutes at 20° C., and the protein concentration was determined in the supernatants.

D. Results

The first series of results concerns the Promilk 852 B milk proteins and the UF pea proteins, taken alone and in the assembly.

Table 2 presents the degree of solubility and dispersibility of the assemblies obtained with the three pH strategies. The control (initial) corresponds to the assaying of the protein concentration on the crude assembly without prior centrifugation.

Table 3 presents the solubility of the proteins alone, and of the assembly for the three assembly pHs tested.

TABLE 2

Dispersibility and solubility of the assemblies obtained with the three pH strategies

| | Initial (32 mg 852 B + 8 mg UF pea/ml) | 300 g (dispersibility) | 5000 g (solubility) |
|---|---|---|---|
| pH 7 | 100% | 100% | 100% |
| pH 5.8 | 100% | 100% | 80% |
| pH 5.8 then raised to 6.9 | 100% | 100% | 75% |

TABLE 3

Concentration (mg/ml) of soluble proteins in the initial dispersions and the mixture

| | pH 7 | ph 5.8 | pH 5.8 to 6.9 |
|---|---|---|---|
| Promilk 852 B (mg/ml) | 32 | 25 | 27 |
| UF pea (mg/ml) | 4 | 1 | 3 |
| Promilk 852 B + UF assembly (mg/ml) | 39 | 32 | 30 |
| Concentration obtained/initial concentration * | 0.975 | 0.80 | 0.75 |

* The initial concentration is 40 mg/ml (32 mg/ml of Promilk 852 B and 8 mg/ml of UF pea)

The above results show that the solubility (soluble fraction after 5000 g for 10 minutes) of the proteins in the pea/casein assemblies is dependent on the mixing strategy.

The assembly at pH 5.8 raised to 6.9 results in final soluble protein concentrations equal to the addition of the concentrations of soluble proteins in the raw materials (UF proteins and caseins).

With regard to the assemblies at pH 7 and pH 5.8, the soluble protein concentration of the assembly is greater than the sum of the concentrations of soluble proteins in the raw materials (Promilk 852 B and UF proteins). In this case, the solubility of the proteins is improved in these two assemblies.

This perfectly demonstrates that there is a synergistic effect at the level of the solubility of the proteins in the assemblies at pH 5.8 and pH 7.

The second series of results concerns the Promilk 852 B caseins and the Nutralys® S85 M pea proteins taken alone and in the assembly.

The same tables are presented.

TABLE 4

Dispersibility and solubility of the assemblies obtained with the three pH strategies

| | Initial (32 mg 852 B + 8 mg Nutralys pea/ml) | 300 g (dispersibility) | 5000 g (solubility) |
|---|---|---|---|
| pH 7 | 100% | 98% | 95% |
| pH 6 | 100% | 98% | 98% |
| pH 6 then raised to 6.9 | 100% | 98% | 98% |

TABLE 5

Concentration (mg/ml) of soluble proteins in the initial dispersions and the mixture

| | pH 7 | ph 5.8 | pH 5.8 to 6.9 |
|---|---|---|---|
| Promilk 852 B (mg/ml) | 32 | 25 | 27 |
| Nutralys pea (mg/ml) | 2 | 0 | 2 |
| Promilk 852 B + Nutralys assembly (mg/ml) | 38 | 38 | 39 |
| Concentration obtained/initial concentration * | 0.95 | 0.95 | 0.975 |

* The initial concentration is 40 mg/ml (32 mg/ml of Promilk 852 B and 8 mg/ml of Nutralys pea).

The above results show that the solubility (soluble fraction after 5000 g for 10 minutes) of the proteins in the pea/casein assemblies is dependent on the mixing strategy.

In the three assemblies, a clear improvement in the solubility of the proteins is to be noted.

Indeed, the concentrations of soluble proteins in the assemblies are higher than the sum of the concentrations of soluble proteins in the raw materials (39>27+2, 38>25+0 and 38>32+2).

This perfectly demonstrates that there is a synergistic effect at the level of the solubility of the proteins in the three cases.

The third series of results concerns the Promilk 852 B caseins and the pea protein flocculate taken alone and in the assembly.

The pea protein flocculate has a pH of 4.5. It was therefore mixed with the 852 B caseins according to the procedure described below, and the final assembly has a pH of 6.5.

Assembly Strategy:

The pea proteins in the flocculate are at a concentration of 16 mg/ml and pH 4.5.

The caseins are at a concentration of 64 mg/ml and pH 7.
50/50 (v/v) mixing of the pea proteins with the dairy proteins.
Final pH of the assembly: 6.5.
Homogenization by means of two passes at 300 bar at ambient temperature.
The same tables are presented.

TABLE 6

Dispersibility and solubility of the assemblies obtained with the various pH strategies

|  | Initial (32 mg 852 B + 8 mg flocculate/ml) | 300 g (dispersibility) | 5000 g (solubility) |
|---|---|---|---|
| pH 6.5 | 100% | 100% | 100% |
| pH 7 | 100% | 100% | 100% |
| pH 5.8 | 100% | 100% | 80% |
| pH 5.8 then Raised to 6.9 | 100% | 100% | 100% |

TABLE 7

Concentration (mg/ml) of soluble proteins in the initial dispersions and the mixture

|  | pH 6.5 | pH 7 | pH 5.8 | pH 5.8 to 6.9 |
|---|---|---|---|---|
| Promilk 852 B (mg/ml) | 32 | 32 | 25 | 27 |
| Flocculate (mg/ml) | 0 | 2 | 0 | 3 |
| 852 B + flocculate assembly (mg/ml) | 40 | 40 | 32 | 40 |
| Concentration obtained/initial concentration * | 1 | 1 | 0.8 | 1 |

* The initial concentration is 40 mg/ml (32 mg/ml of Promilk 852 B and 8 mg/ml of flocculate).

The above results show that the solubility (soluble fraction after 5000 g for 10 minutes) of the proteins in the pea/casein assemblies is improved whatever the assembly strategy (pH 6.5, pH 7, pH 5.8 and pH 5.8 with pH being raised to 6.9).

It emerges very clearly from the latter example that there is indeed a synergistic effect in the assemblies produced between dairy proteins and the vegetable proteins according to the present invention.

Example 5

Technological Aptitude of the Protein Assemblies Obtained

In order to study the technological aptitudes of the protein assemblies, we worked on an 80/20 (casein/pea) ratio in order to achieve a protein concentration of 40 mg/ml in the assemblies.

A. Screening of the Optimal Coagulation Conditions (GDL and Rennet Concentration)

Glucono-delta-lactone (GDL) is a cyclic ester of D-gluconic acid. The latter is obtained by fermentation of glucose and then crystallized in GDL form. GDL is an acidogenic agent which allows gradual acidification, unlike the other food acids. It is used in cheeses, meat-based products, tofu, and baked products.

Rennet is a coagulatant of animal origin that is extracted from the fourth stomach (abomasum) of calves and of young cattle. It consists of active enzymes called chymosin. It is intended for the dairy industry for the coagulation of milk for cheese production.

To do this, we worked on a dairy reference Promilk 852 B at 40 mg/ml and on the UF+852 B mixtures at pH 7 and 5.8 raised to 6.9.

For each of these fractions, the required concentrations of GDL to achieve a pH of 4.6 and of rennet were determined with and without heat treatment (70° C. for 15 seconds for rennet and 92° C. for 5 minutes for GDL).

The optimal GDL concentration to achieve a pH of 4.6 after 6 hours at 23° C. is 1.9% (W/V) for all the protein fractions.

The rennet concentration which coagulates the proteins at 33° C. is 1/400 (V/V) for all the protein fractions.

B. GDL Coagulation

The protein fraction coagulation kinetics by rheology were monitored.

The resistance of the paste continuously changes before and after these reference points. The coagulation can be demonstrated by dynamic rheometry. Indeed, if a sinusoidal strain sufficiently weak so as not to destroy the paste is applied to the latter, and the stress induced in the material by the strain is measured, it is possible to measure the elastic modulus (G') expressing the solid nature of the material and the viscous modulus (G") expressing the liquid nature of the material as a function of time. After the end of coagulation, the curd goes from a liquid nature G">G' to a solid nature G'>G". This rapid transition is due to the coagulation of the protein fractions.

The change in the G' and G" moduli as a function of time at a strain of 1% and a frequency of 1% were determined. These monitorings were carried out in striated plate-plate geometry. The appearance of the coagulation curves of the mixtures is similar to that of milk, but the final moduli are quite different.

The change in the pH was also monitored throughout the coagulation (6 hours).

A visual assessment of the cohesion of the gels was also carried out.

Table 8 below summarizes the values of the final G' moduli and the coagulation pHs and also the Tan delta max values for the heat-treated fractions.

TABLE 8

|  | Without heat treatment | | Heat treatment at 92° C. for 5 min | | |
|---|---|---|---|---|---|
|  | Final G' (Pa) | Gelling pH | Final G' (Pa) | Gelling pH | Tan delta max |
| 852 B 4% (40 mg/ml of proteins) | 173 | 5.6 | 272 | 5.3 | 0.52-pH 5.15 |
| UF + 852 B assembly pH 7 | 159 | 5.9 | 242 | 5.4 | 0.43-pH 5.15 |
| UF + 852 B assembly pH 5.8 to 6.9 | 201 | 5.6 | 147 | 5.3 | 0.47-pH 5.17 |
| Nutralys + 852 B assembly pH 7 | 200 | 5.5 | 420 | 5.4 | 0.46-pH 5.2 |
| Nutralys + 852 B assembly pH 6 to 6.9 | 392 | 5.5 | 413 | 5.2 | 0.46-pH 5.2 |

TABLE 8-continued

| | Without heat treatment | | Heat treatment at 92° C. for 5 min | | |
|---|---|---|---|---|---|
| | Final G' (Pa) | Gelling pH | Final G' (Pa) | Gelling pH | Tan delta max |
| Flocculate + 852 B assembly pH 7 | 420 | 5.6 | 460 | 5.5 | 0.48- pH 5.3 |
| Flocculate + 852 B assembly pH 5.8 then raised to 6.9 | 527 | 5.6 | 231 | 5.2 | 0.48- pH 5.3 |

C. Conclusions Regarding the GDL Coagulation

The Nutralys+Promilk 852 B assembly: the final G' moduli are multiplied by a factor of 2 compared with those of 852 B 4%, in particular regarding the combinations with heat treatment.

The flocculate+852 B assembly: the final G' moduli are multiplied by a factor of 2 compared with those of 852 B 4%, in particular for the combinations without heat treatment.

Bringing together pea proteins (UF, Nutralys and flocculate) and casein (Promilk 852 B) in an 80/20 proportion makes it possible to obtain GDL gels with final G' values greater than those of the dairy protein (Promilk 852 B 4%).

D. Rennet Coagulation

In the cheese industry which is based on rennet coagulation, the quality of a gel is judged according to its texture (rheological characteristics) and also with regard to the protein recovery (the least possible loss in the exudate).

During the rennet coagulation kinetics measurements, it was demonstrated that the milk protein/vegetable protein assemblies according to the present invention had advantageous coagulation kinetics. Indeed, the coagulation kinetics of the milk protein/vegetable protein assemblies according to the present invention are comparable to the coagulation kinetics of the dairy proteins.

Bringing together pea proteins and milk proteins according to the present invention does not therefore disrupt the rennet coagulation kinetics.

As shown in FIG. 1, the provision of pea proteins in various forms and according to various assembly processes results in protein losses comparable to those obtained with the protein solution based on Promilk 852 B, under the laboratory operating conditions.

The invention claimed is:

1. A process for obtaining an assembly of a pea protein and at least one casein consisting of the steps of:
    obtaining an aqueous composition comprising a pea protein;
    lowering the pH of said composition comprising a pea protein to a value less than or equal to 2.5 so as to obtain an acidified composition, wherein the lowering of the pH denatures the pea protein;
    obtaining an aqueous composition comprising at least casein, wherein the casein is not denatured;
    introducing the aqueous composition comprising at least casein into said acidified composition so as to obtain a mixture;
    resting the mixture, during which no treatment is applied;
    homogenizing the mixture at a temperature of between 4° C. and 35° C. the mixture obtained; and
    raising the pH of said homogenized mixture to a value between 6.9 and 7.5 so as to obtain said assembly, wherein the pea protein and the casein protein are folded on themselves and between themselves so as to adopt a three-dimensional supramolecular structure.

2. The method of claim 1 wherein no pH adjustments are made to the aqueous composition comprising at least casein.

* * * * *